United States Patent [19]
Champetier

[11] Patent Number: 5,196,901
[45] Date of Patent: Mar. 23, 1993

[54] DISCRIMINATING SURFACE CONTAMINATION MONITOR

[75] Inventor: Robert J. Champetier, San Pedro, Calif.

[73] Assignee: EOS Technologies, Inc., Santa Monica, Calif.

[21] Appl. No.: 748,688

[22] Filed: Aug. 22, 1991

[51] Int. Cl.$^5$ .................... G01N 21/00; H01J 5/16
[52] U.S. Cl. .................... 356/237; 356/239; 356/338; 250/227.23; 250/223 B
[58] Field of Search ............... 356/237, 239, 240, 337, 356/338, 343; 250/223 B, 227.23, 227.29, 227.21, 572, 561, 562

[56] References Cited

U.S. PATENT DOCUMENTS

| | | | |
|---|---|---|---|
| H376 | 12/1987 | Bremer | 356/239 |
| 3,394,263 | 7/1968 | Baker | 250/223 B |
| 3,894,806 | 7/1975 | Remy et al. | 250/223 B |
| 3,988,068 | 10/1976 | Sprague | 356/239 |
| 4,456,374 | 6/1984 | Langberg | 356/237 |
| 4,629,318 | 12/1986 | Malek et al. | 356/237 |
| 4,808,813 | 2/1989 | Champetier | 250/227.23 |

FOREIGN PATENT DOCUMENTS

| | | | |
|---|---|---|---|
| 0044587 | 4/1979 | Japan | 356/239 |
| 0085209 | 6/1980 | Japan | 356/237 |

*Primary Examiner*—Richard A. Rosenberger
*Assistant Examiner*—Hoa Q. Pham
*Attorney, Agent, or Firm*—Kirkpatrick & Lockhart

[57] ABSTRACT

A surface contamination monitor which discriminates between different types of surface contamination and irregularities is provided with a horizontal sensing plate, a light detector positioned under the plate, a narrow bandpass filter disposed between the plate and the detector, and optical lenses. At one end of the sensing plate is included three laser diodes, while at the other end is located a coupling prism. Beams from the laser diodes strike the coupling prism and are directed at different angles so as to either strike the exposed surface of the sensing plate or become trapped within the sensing plate. Variations in the reactions of the different beams to different contaminants and irregularities on the exposed sensing plate surface allow the light detector to discriminate between dust, molecular films, and scratches and craters on the exposed surface.

5 Claims, 1 Drawing Sheet

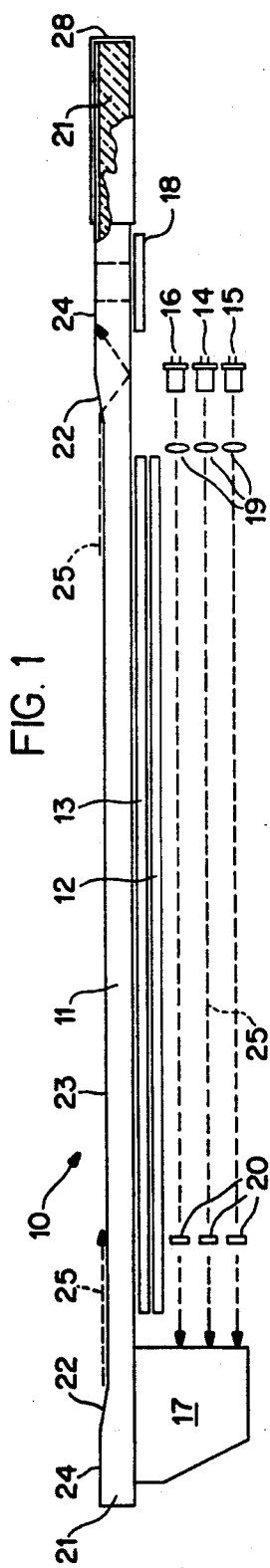
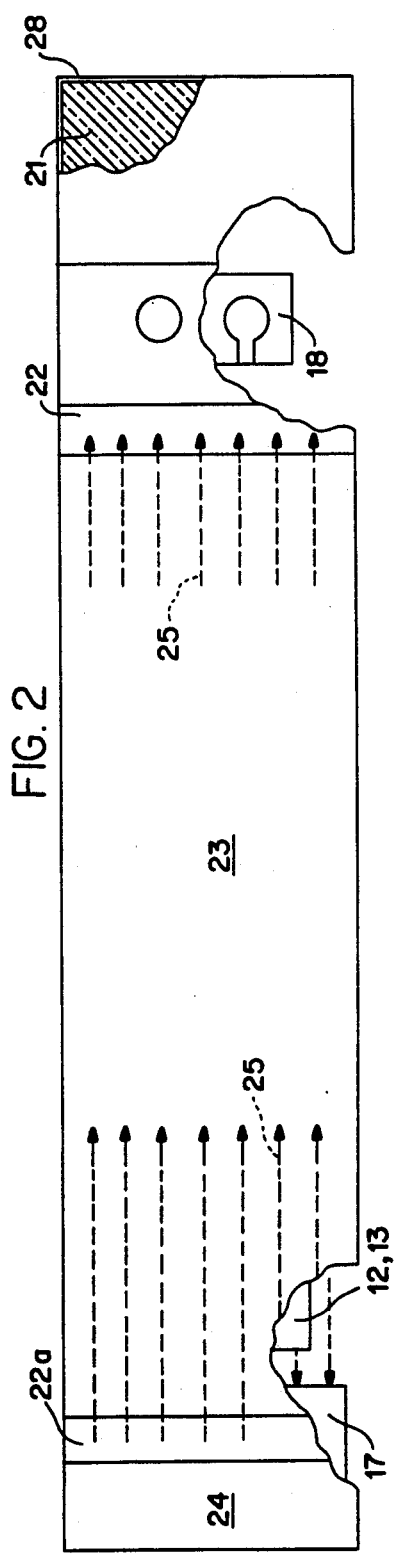
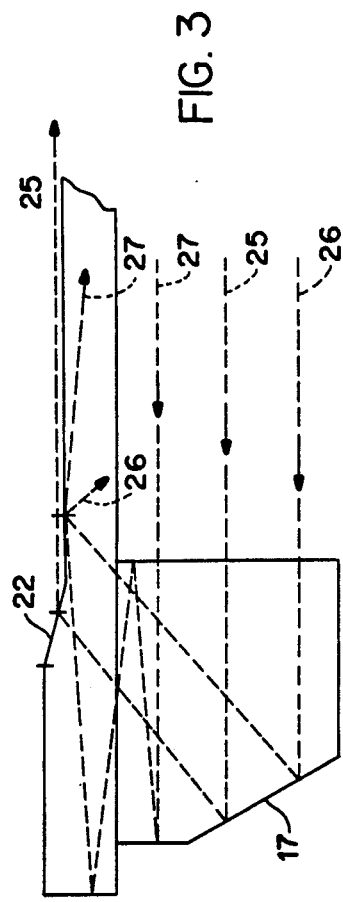

5,196,901

DISCRIMINATING SURFACE CONTAMINATION MONITOR

BACKGROUND OF THE INVENTION

1. Field of the Invention

This invention relates generally to devices used for detection of contaminations deposited on optical elements. More specifically it relates to an improvement made on the applicant's prior U.S. Pat. No. 4,808,813 granted Feb. 28, 1989 entitled "Self Contained Surface Contamination Sensor for Detecting External Particulate and Surface Discontinuities".

Prior Art: In the applicant's prior patent, a sensor is disclosed that uses two diodes. Contamination, either in the form of particulate matter (for example: dust and non-wetting liquid) or surface discontinuities, such as a smooth film or cratering, is collected on an exposed glass plate. Illumination at an angle incident with respect to a surface of the glass plate causes the particulate matter to scatter the light beam from one of the diodes. The light beam from the other diode illuminates the inside volume of the glass plate, causing light to scatter from the surface discontinuities. Either source of light scattering is detected by an optically sensitive detector positioned below the glass plate. A bandpass filter between the glass plate and the detector rejects spurious radiation. Although the device accomplishes its intended task of detecting external particulate and surface discontinuities, it does not, however, distinguish which type of contamination has been deposited, so that the device is accordingly in need of further improvement.

BRIEF SUMMARY OF THE INVENTION

Therefore it is a principal object of the present invention to provide a Discriminating Surface Contamination Monitor which additionally identifies also the type of the accumulated contamination.

More specifically, another object is to provide a Discriminating Surface Contamination Monitor which permits discrimination between three basic types of contamination: (1) dust (2) molecular deposits and (3) cratering, erosion or scratching, such as by micrometeorite impingement or handling damage.

Another, object is to provide a Discriminating Surface Contamination Monitor which give electrical signals that tells how much contamination has accumulated.

Yet a further object is to provide a Discriminating Surface Contamination Monitor that may be monitored either continuously by an operator or be interrogated when desired.

Other objects are to provide a Discriminating Surface Contamination Monitor which is simple in design, inexpensive to manufacture, rugged in construction, easy to use and efficient in operation and use.

These and other objects will be readily evident upon a study of the following specification and the accompanying drawing.

BRIEF DESCRIPTION OF THE DRAWINGS

FIG. 1 is a side elevational view of the invention.

FIG. 2 is a top view thereof shown partly broken away so to illustrate underneath structure.

FIG. 3 is an enlarged diagram showing beam paths through a prism and one end of a sensing plate.

DETAILED DESCRIPTION OF A PREFERRED EMBODIMENT

Referring now to the drawing in greater detail, the reference numeral 10 represents a discriminating surface contamination monitor according to the present invention and which is placed entirely into the environment that is intended to be monitored, such as a vacuum chamber, test apparatus or space craft surface so as to be exposed to any contamination therein.

The monitor comprises a sensing plate 11, a light detector 12 therebelow, a narrow bandpass filter, 13 sandwiched therebetween, three laser diodes 14, 15 and 16, a coupling prism 17, and quartz crystal microbalance 18 together with associated optical lens and electronic components. The optical lens include a plurality of glass cylindrical lens 19 and holographic cylindrical lens 20 along a path for light beams between the diodes and the coupling prism. All the beams traverse through the prism and then aim at the plate.

The coupling prism is located under one end of the sensing plate 11 and abuts the underside thereof. The sensing plate is made of glass, is transparent, and being shown in a horizontal position in the drawing. It is flat throughout its length except for upwardly thickened flat portions 21 at each opposite end. As shown in FIG. 1, a facet 22 at an inclined angle connects between the upper face 23 of sensing plate 11 and the upper face 24 of the thickened portions 21 at each end.

Light beams 25, 26 and 27 from the diodes 14, 15 and 16 are hereinafter termed as the first, second and third beam respectively. In operative use of the device, contamination accumulations may be read by turning on the lasers one at a time and taking a detector reading each time. Each of the three beams follows a different path.

The first beam 25 is polarized parallel to a plane of incidence of the sensing plate and exits the plate at a correct angle from the first facet 22 that allows the beam to emerge for grazing the plate face 23 and after traveling thereacross, the beam is disposed at the other facet 22. Any dust on the surface causes some of the beam to be scattered in all directions. A portion of that scattered light enters the plate, traverses it and impinges on the light detector 12 therebeneath.

The second beam 26 is made to enter the sensing plate so as to bounce within the plate and remain trapped therewithin by means of a total internal reflection. Dust particles contact the plate only at very small spots, so that negligible internal light from the second beam couples with the dust. Localized molecular film or films formed by the action of solar ultraviolet light, however, does contact the plate and can scatter the light from the second beam, which then causes a signal to occur at the detector 12.

The third beam 27 also travels within the sensing plate and is also trapped by total internal reflection, but it grazes the exposed surface of the plate. This orientation renders it insensitive to molecular films.

Beams 2 and 3 are both affected by scratches and craters in the plate, but only beam 2 responds to molecular films. Beam 1 is insensitive to such films or to scratches. However, beam 1 will respond to molecular contamination in the form of droplets on the surface, just as if they were dust. To help discriminate between molecular contamination in the form of films in closed contact versus droplets barely in contact with the plate, the present invention includes a quartz crystal microbalance 18 which responds mainly to films. This microbalance is an established device, available commercially, and very small in size. It measures the mass of a film deposited on its surface.

Also shown in FIGS. 1 and 2, the opposite end of the plate, re-entered by the beam, is blackened at 28 to absorb laser beams.

The present invention incorporates advantageous key features when compared to the applicant's prior patent. These comprise: (a) the use of a third beam to provide discrimination between molecular films and cratering; (b) combination with a quartz microbalance to differentiate between molecular droplets and films; (c) a means of causing beam 1 to graze the outer surface with high efficiency; (d) a means to depose of beam I at the other end of the plate, so as not to impinge on other objects than the device; and (e) a smooth outer, exposed surface, with no protrusions for handling beam 1, which renders the invention relatively immune to damage or misalignment, and makes it easily cleanable.

While various changes may be made in the detail construction, it is understood that such changes will be within the spirit and scope of the present invention as is defined by the appended.

What we claim is:

1. A discriminating surface contamination monitor, comprising in combination; a horizontal sensing plate, a coupling prism abutted under one end thereof, three laser diodes for directing light beams into said prism and radiating into said sensing plate, a light detector under said plate, a bandpass filter therebetween, means for a beam from a first of said diodes to emerge from said sensing plate and graze and outer surface thereof for detecting dust upon said plate surface, means for a beam from a second of said diodes to principally detect molecular film deposit on said plate, and means for a beam from a third of said diodes to detect craters in said plate surfaces; and the first said means including a quartz crystal microbalance located beneath said sensing plate for detecting molecular contamination.

2. The combination as set forth in claim 1, wherein a first inclined facet is located near one end of said sensing plate for emerging first diode beam externally from said sensing plate.

3. The combination as set forth in claim 2, wherein said first diode beam is polarized parallel to plane of incidence respective to said sensing plate.

4. The combination as set forth in claim 3, wherein second inclined facet is located near an apposite end of said sensing plate for re-entry of said external beam into said sensing plate.

5. The combination as set forth in claim 4, wherein each said facet is between an upwardly thickened end portion at each end of said sensing plate and thinner flat central portion therebetween having said surface being grazed.

* * * * *

UNITED STATES PATENT AND TRADEMARK OFFICE
CERTIFICATE OF CORRECTION

PATENT NO. : 5,196,901
DATED : March 23, 1993
INVENTOR(S) : Robert J. Champetier It is certified that error appears in the above-identified patent and that said Letters Patent is hereby corrected as shown below:

Col. 3, line 14, delete "I" and
substitute therefor --1--.

Signed and Sealed this

Fourth Day of January, 1994

Attest:

BRUCE LEHMAN

*Attesting Officer*    *Commissioner of Patents and Trademarks*